US00PP35062P2

(12) United States Plant Patent
Takahashi et al.

(10) Patent No.: US PP35,062 P2
(45) Date of Patent: Mar. 21, 2023

(54) ***GENTIANA* PLANT NAMED 'ASHIRO 29-2005'**

(50) Latin Name: ***Gentiana* L. hybrid**
Varietal Denomination: Ashiro 29-2005

(71) Applicant: HACHIMANTAI CITY, Hachimantai (JP)

(72) Inventors: Ryo Takahashi, Hachimantai (JP); Yutaro Takamura, Morioka (JP); Rina Suzuki, Hachimantai (JP); Takashi Hikage, Morioka (JP)

(73) Assignee: HACHIMANTAI CITY, Hachimantai (JP)

( * ) Notice: Subject to any disclaimer, the term of this patent is extended or adjusted under 35 U.S.C. 154(b) by 0 days.

(21) Appl. No.: 17/556,569

(22) Filed: Dec. 20, 2021

(51) Int. Cl.
*A01H 5/02* (2018.01)
*A01H 6/40* (2018.01)

(52) U.S. Cl.
USPC ..... Plt./433
CPC ..... *A01H 6/40* (2018.05)

(58) Field of Classification Search
USPC ..... Plt./433
CPC ..... A01H 5/02
See application file for complete search history.

*Primary Examiner* — Kent L Bell
(74) *Attorney, Agent, or Firm* — Seckel IP, PLLC

(57) ABSTRACT

A new variety of *Gentiana* L. plant (Japanese gentian) which is a double flower type and has about 1-2 (1.5 on average) side shoots with only one node.

4 Drawing Sheets

Common name: Japanese gentian.
Botanical classification: *Gentiana* L. hybrid.
Variety denomination: 'Ashiro 29-2005'.

BACKGROUND OF THE NEW VARIETY

The present invention relates to a new and distinct variety of Japanese gentian, *Gentiana* L., which has been given the variety denomination 'Ashiro 29-2005'.

This new gentian is a double flower type and has about 1-2 (1.5 on average) side shoots with only one node. It is adapted for use as cut flowers or pot flowers.

ORIGIN OF THE VARIETY

The variety resulted from a multiple-step cross-breeding program starting from a group of unpatented varieties. The ancestor varieties were unpatented strains owned by the applicant, having the company-internal names: '17INP' which belongs to the species *Gentiana triflora*, and '26-904', '12-316-3', '17SUP', and '8-130SP6A1', which belong to the species *Gentiana scabra*. Group crosses and/or self-crosses with a single individual were performed. The program had seven steps, as shown in the map of FIG. 6, which also indicates the company-internal names of the intermediary, unpatented strains. At each step, the individuals with good plant and flower shape were selected. The corresponding species identification is ((*scabra* x *triflora*) x *scabra*)) x ((*scabra* x *triflora*) x *scabra*)).

With respect to the direct parents '28-2001' and '27-836-18', the instant variety 'Ashiro 29-2005' has a triploid and double-flowered flower type, whereas '28-2001' has tetraploid and single-flowered flower type, and '27-836-18' has diploid and double-flowered flower type.

The multiple-step cross-breeding program was performed over multiple growing seasons up to 2018; in September 2018, selection of the variety was performed. We asexually reproduced the variety by vegetative reproduction through cuttings, tissue culturing via lateral bud culture, and in October 2020, the new variety was found to be stable and asexually reproduced true to type in successive generations.

The variety was developed and propagated in Iwate, Japan.

The variety can be propagated by cutting (optimal timing is mid-February) and/or tissue culturing via lateral bud culture.

Cultivation of the variety does not require particular conditions. Maintenance and storage method of the plant material can be by tissue culture via lateral bud culture.

The variety is adapted for use as cut flowers or pot flowers.

SUMMARY OF THE VARIETY

The variety is distinguished by double flower type and has about 1-2 (1.5 on average) side shoots with only one node, as compared to 'Shine Blue Ashiro' variety which is single flower type and has about 6 side shoots with only one node. 'Shine Blue Ashiro' is unpatented.

A comparison with 'Shine Blue Ashiro' variety is presented as follows in Table 1:

TABLE 1

| | 'Shine Blue Ashiro' | 'Ashiro 29-2005' |
|---|---|---|
| Flower type | Single | double |
| Number of side shoots with only one node | 6 | 1-2 (1.5 on average) |

Additional distinguishing characteristics of the 'Ashiro 29-2005' plant are the five (5.0 on average) lobes of the paracorolla, and the strong purplish-blue color (94B on R.H.S. Colour Chart) of the secondary lobes with acute apex in-between the main lobes of the corolla.

BRIEF DESCRIPTION OF THE DRAWINGS

In the accompanying drawings, which are as nearly true as is reasonable possible to make in a color illustration of this type.

Figure 1:
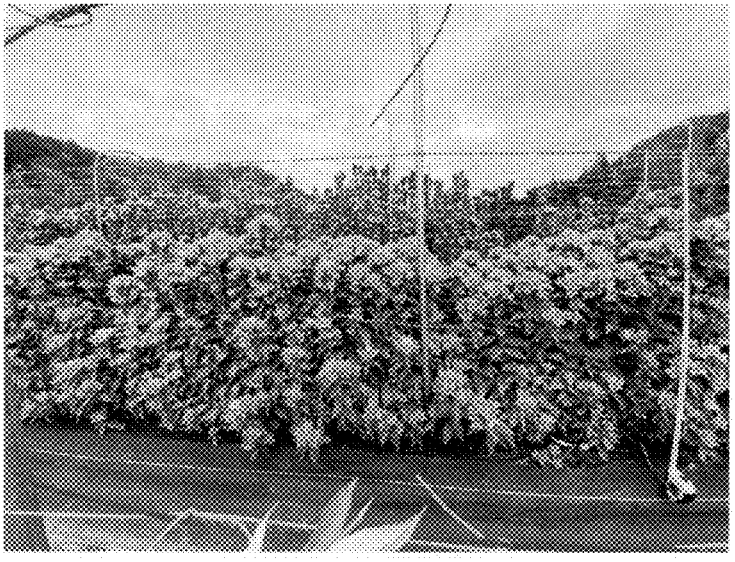
FIG. 1 is a color photograph showing the 'Ashiro 29-2005' plant as grown in a culturing bed.
Figure 2:
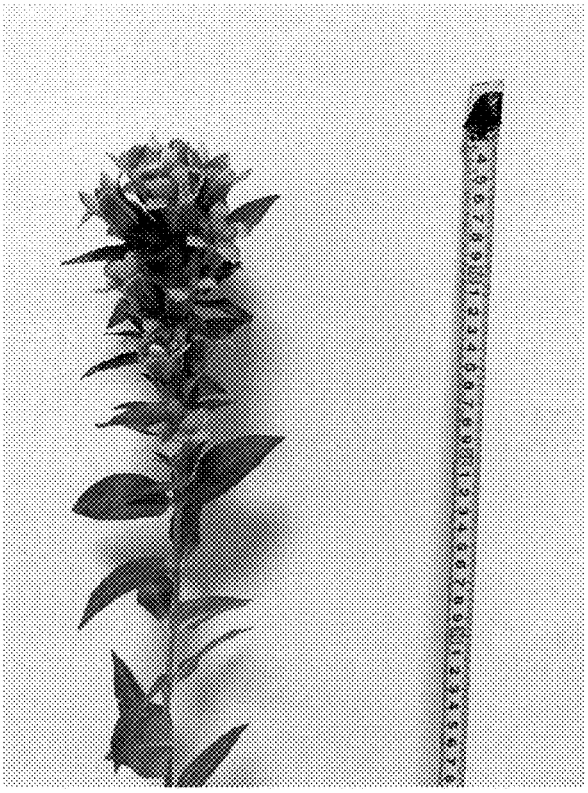
FIG. 2 is a color photograph showing flowers of the 'Ashiro 29-2005' plant.
Figure 3:
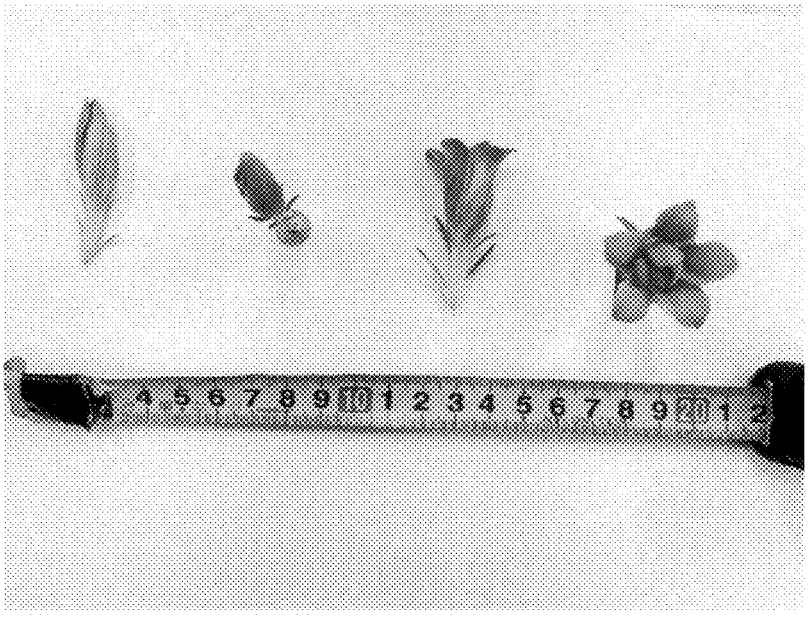
FIG. 3 is a color photograph showing flowering stages of flowers of the 'Ashiro 29-2005' plant.
Figure 4:
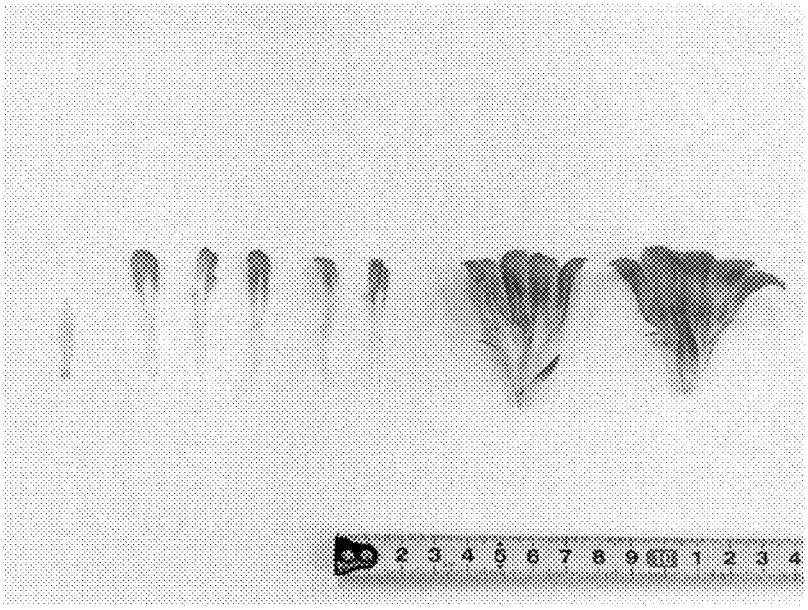
FIG. 4 is a color photograph showing petals of flowers of the 'Ashiro 29-2005' plant.
Figure 5:
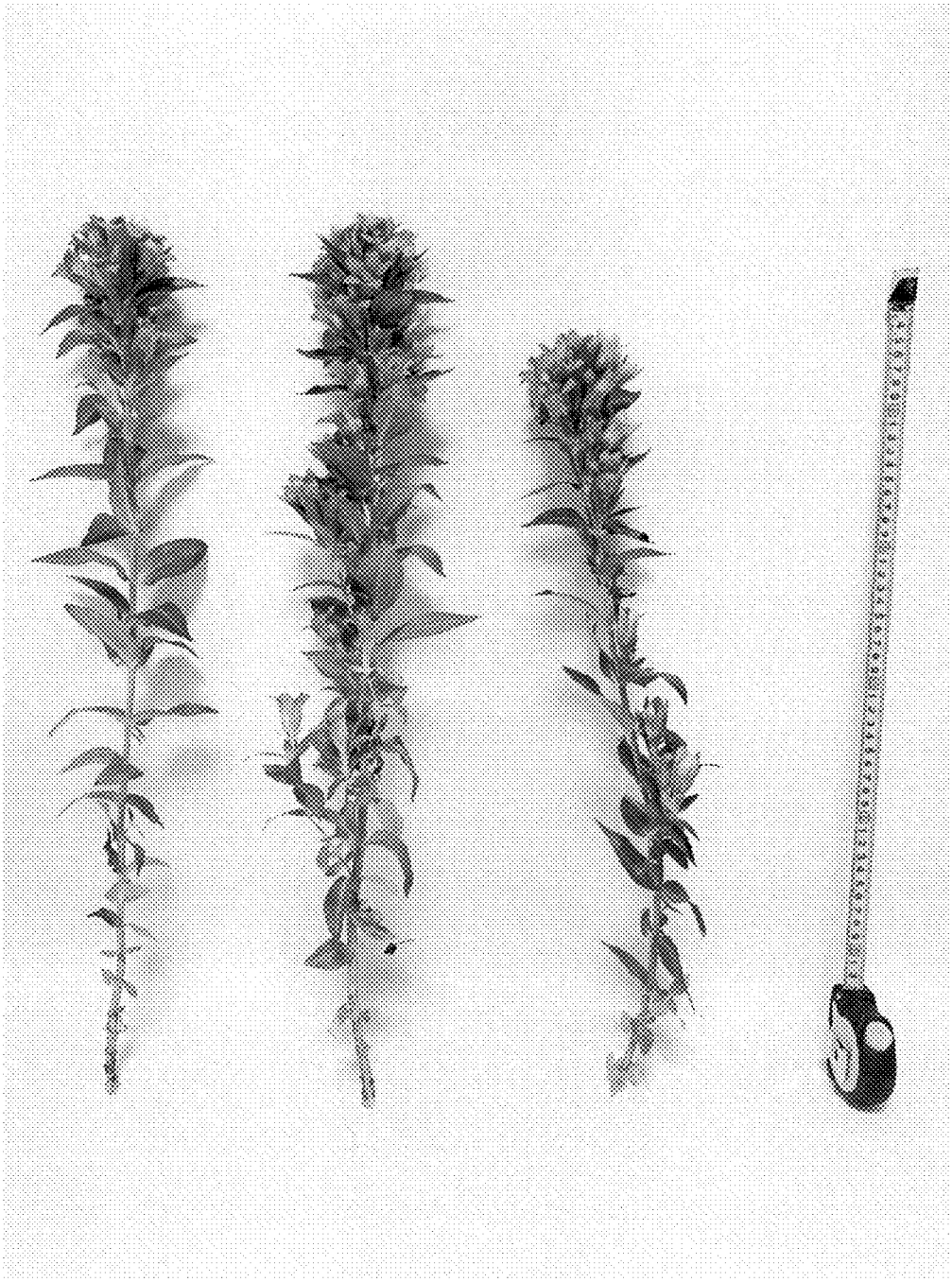
FIG. 5 is another color photograph showing flowers of the 'Ashiro 29-2005' plant.
Figure 6:
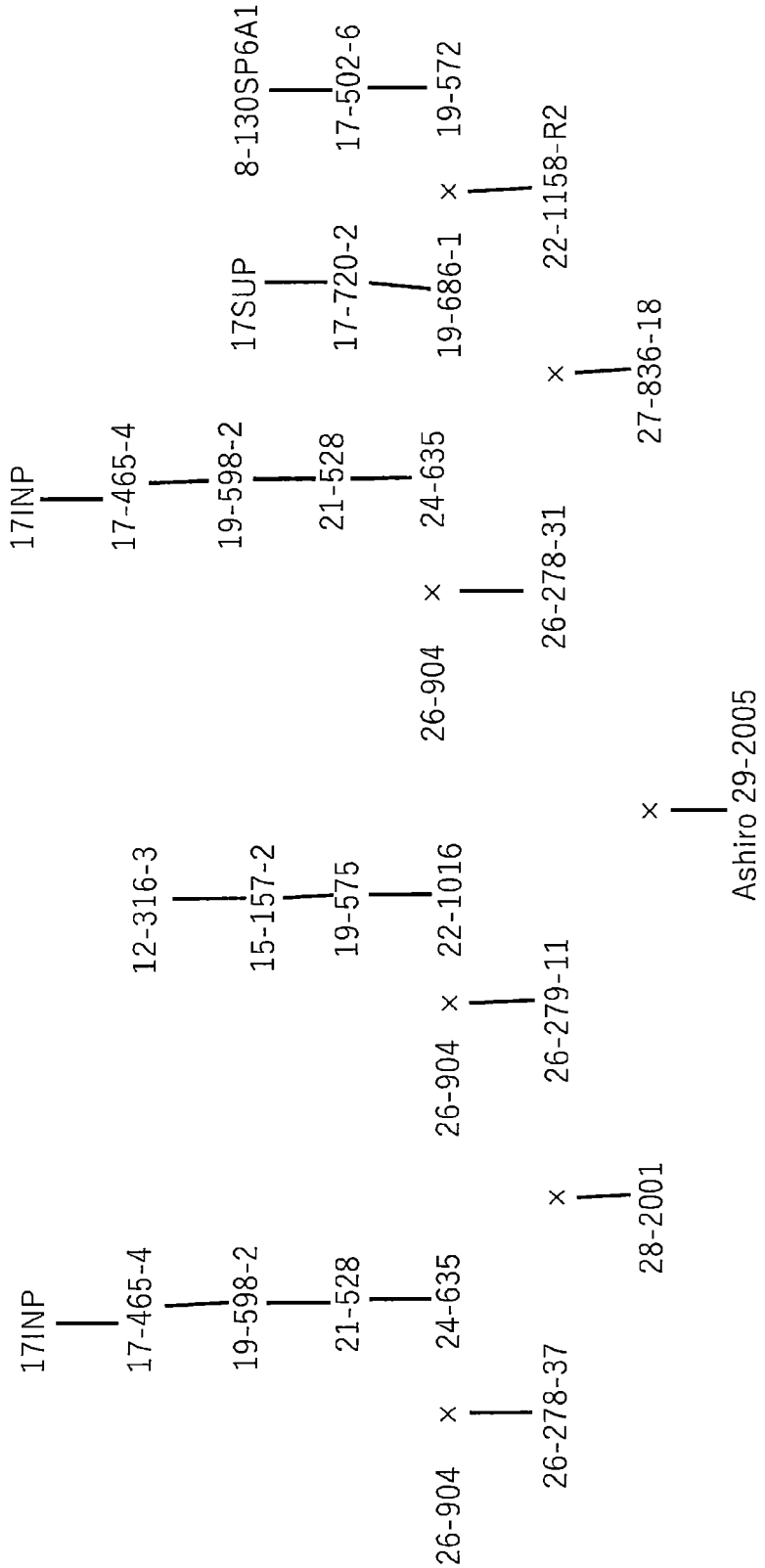
FIG. 6 is a map showing the steps of the cross-breeding program from which the variety was obtained.

Due to chemical and/or digital development, processing and printing, the plants or portions of plants depicted in the photographs may or may not be precisely accurate, when compared to the actual botanical specimens.

DETAILED DESCRIPTION OF THE INVENTION

The plants in the botanical description below and shown in the Figures were grown in Iwate, Japan. The plants were collected in October 2020 at age 16 months.

Colors are given according to The 2015 R.H.S. Colour Chart.

BOTANICAL DESCRIPTION

TABLE 2

| | | |
|---|---|---|
| Stem | Length: | 57.8 cm |
| | Thickness (main flowering stem): | 4.1 mm |
| | Number of flowering stems per plant (average): | 27.6 |
| | Texture: | smooth |
| | Color: | light yellow green (145B on RHS Colour Chart) |
| | Anthocyanin coloration at two thirds from base: | absent |
| | Number of internodes longer than 5 mm (average): | 17.8 |
| | Length of internode in central third: | 3.4 cm |
| | Side shoots: | present |
| | Number of side shoots with only one node (average): | 1.5 |
| | Number of side shoots with more than one node (average): | 4.0 |
| | Length of side shoots (average): | 21.8 cm |
| | Diameter of side shoots (average): | 2.5 mm |
| | Texture of side shoots: | smooth |
| | Color of side shoots: | light yellow green (145C on RHS Colour Chart) |
| | Position of longest leaf: | in central third |
| Leaf | Length: | 7.2 cm |
| | Leaf arrangement: | opposite leaf arrangement |
| | Leaf attachment: | sessile |
| | Leaf apex: | acuminate |
| | Leaf margin: | entire |
| | Leaf base: | rounded |
| | Leaf texture (inner side): | smooth |

TABLE 2-continued

| | | |
|---|---|---|
| | Leaf texture (outer side): | smooth |
| | Leaf color (inner side): | moderate olive green (137A on RHS Colour Chart) |
| | Leaf color (outer side): | light yellow green (138D on RHS Colour Chart) |
| | Leaf venation pattern: | parallel venation (three lines) |
| | Leaf venation color: | light yellow green (150D on RHS Colour Chart) |
| | Width: | 3.1 cm |
| | Shape: | lanceolate |
| | Shape in cross section: | folded upwards |
| | Shape in longitudinal section: | convex |
| | Twisting: | absent |
| | Number of conspicuous veins: | 3 |
| | Anthocyanin coloration: | present, dark greyish red (N186C on RHS Colour Chart) |
| Inflorescence | Distribution of flowers: | clustered |
| | Position of flowers: | terminal and axillary |
| | Number of inflorescences per plant per season (average): | 197.3 |
| Plant: | Number of terminal flowers (average): | 10.7 |
| | Typical growth habit: | erect |
| | Plant height (average): | 57.8 cm |
| | Plant spread (average): | 43.0 cm |
| | Plant shape: | erect |
| | Number of flowers per inflorescence: | top: 10.7<br>others: 2.8 |
| | Number of flowers at central flowering node (average): | 2.8 |
| | Number of flowering node: | 4.6 |
| Flower bud (about 4 days before flowering) | Shape of bud: | narrow oval |
| | Length of bud (average): | 39.5 mm |
| | Diameter of bud (average): | 9.3 mm |
| | Color of bud: | light purple (N82C on RHS Colour Chart) |
| Flower | Type: | double |
| | Time of flowering: | early October |
| | Flower longevity (potted plant): | 11 days |
| | Flower longevity (cut flower): | 8 days |
| Corolla | Depth: | 47.1 mm |
| | Diameter at middle third: | 14.8 mm |
| | Shape: | campanulate |
| | Diameter at top: | 29.5 mm |
| | Curvature of lobes: | reflexed |
| | Margin of lobes: | entire |
| | Texture of lobes: | smooth |
| | Color of outer side of lobes: | very light purple (85C on RHS Colour Chart) |
| | Color of inner side of lobes: | brilliant purplish blue (94C on RHS Colour Chart) |
| | Tube length (average): | 26.7 mm |
| | Tube texture: | smooth |
| | Color of inner side of tube: | very pale purple (85D on RHS Colour Chart) |
| | Color of upper part of inner side of tube: | brilliant purplish blue (94C on RHS Colour Chart) |
| | Color of outer side of tube: | very light purple (85C on RHS Colour Chart) |
| | Color of upper part of outer side of tube: | light purple (85A on RHS Colour Chart) |
| | Streaked pattern on outer side of tube: | present |
| | Color of streaked pattern on outer side of tube: | light purple (N82C on RHS Colour Chart) |
| | Number of lobes: | 5 |
| | Length of lobes: | 10.7 mm |
| | Width of lobes: | 10.2 mm |
| | Shape of lobes: | ovate |
| | Shape of distal end of lobes: | acute |

TABLE 2-continued

| | | |
|---|---|---|
| | Presence of secondary lobes: | present |
| | Shape of secondary lobes: | acute |
| | Shape of secondary lobe apex: | acute |
| | Margin of secondary lobes: | entire |
| | Length of secondary lobes (average): | 2.4 mm |
| | Width of secondary lobes (average): | 3.3 mm |
| | Texture of secondary lobes: | smooth |
| | Color of secondary lobes: | strong purplish-blue (94B on RHS Colour Chart) for both surfaces |
| Paracorolla | Presence of paracorolla: | present |
| | Number of paracorolla lobes (average): | 5.0 |
| Calyx | Anthocyanin coloration: | absent |
| | Length of tube: | 14.5 mm |
| | Diameter of tube: | 5.6 mm |
| | Shape of tube: | funnel-shaped |
| | Texture of tube (inner side): | smooth |
| | Texture of tube (outer side): | slightly wrinkled |
| | Shape of lobe: | narrow lanceolate |
| Sepal | Sepal number: | 5 |
| | Sepal lobe shape: | narrow lanceolate |
| | Sepal length (average): | 13.6 mm |
| | Sepal width (average): | 2.4 mm |
| | Sepal apex: | acute |
| | Sepal margin: | entire |
| | Sepal texture (inner side): | smooth |
| | Sepal texture (outer side): | smooth |
| | Sepal color (inner side): | deep yellowish green (141A on the RHS Colour Chart) |
| | Sepal color (outer side): | light yellow green (138D on the RHS Colour Chart) |

TABLE 2-continued

| | | |
|---|---|---|
| Reproductive organs | Stamens and anther: | stamens are mutated into petals and there is no anther |
| | Pistil number: | 1 |
| | Pistil length (average): | 33.69 mm |
| | Stigma (none) | |
| | Style (none) | |
| | Ovary color: | light yellow green (145C on RHS Colour Chart) |
| Roots | Root shape: | fine and fibrous |
| Pedicel | No pedicel | |
| Peduncle | Peduncle length (average): | 1.1 mm |
| | Peduncle diameter (average): | 2.09 mm |
| | Peduncle texture: | smooth |
| | Peduncle color: | light yellow green (145C on RHS Colour Chart) |

In the above chart, specific numbers correspond to average values.

Other features of the plant are as follows:

Disease resistance: Normal resistance was observed for pests and diseases in Iwate, Japan, using pest control by chemical spraying for gentian.

Cold hardiness: Strong, the variety can withstand winter in Iwate, Japan, including low temperatures of about −10° C. with abundant snow.

Heat tolerance: Normal, the variety can withstand summer in Iwate, Japan, including high temperatures of about 35° C.

Flower fragrance: Absent.

We claim:

1. A new and distinct variety of *Gentiana* plant named 'Ashiro 29-2005', substantially as described and illustrated herein.

* * * * *